United States Patent
Pan (10) Patent No.: US 9,625,394 B1
(45) Date of Patent: Apr. 18, 2017

(54) RAPID IDENTIFICATION METHOD OF ARGYLE DIAMOND'S ORIGIN BY CHARACTRISTIC RAMAN SPECTRA

(71) Applicant: Dong-Shyogn Pan, Taipei (TW)

(72) Inventor: Dong-Shyogn Pan, Taipei (TW)

( * ) Notice: Subject to any disclaimer, the term of this patent is extended or adjusted under 35 U.S.C. 154(b) by 0 days.

(21) Appl. No.: 15/180,103

(22) Filed: Jun. 13, 2016

(51) Int. Cl.
G01N 21/00 (2006.01)
G01N 21/87 (2006.01)
G01N 21/65 (2006.01)

(52) U.S. Cl.
CPC ............ *G01N 21/87* (2013.01); *G01N 21/65* (2013.01); *G01N 2201/06113* (2013.01)

(58) Field of Classification Search
CPC ........ G01N 21/64; G01N 21/65; G01N 21/87; G01N 21/88; G01N 33/381
See application file for complete search history.

(56) References Cited

U.S. PATENT DOCUMENTS

2013/0226646 A1* 8/2013 Watkins ............ G06Q 10/1095
705/7.19

* cited by examiner

*Primary Examiner* — Abdullahi Nur (57) ABSTRACT

The origin of a gemstone often governs its value. Traditional jewelry appraisals attempted the recognition of the origin of a gemstone based on criteria of its physical properties include, but not limited to color, refractive indices, and microstructure. However, these criteria, in addition to its inclusions, are generally failed to resolve the locality and origin of a gemstone without doubt. Through careful examination and compilation of Raman spectroscopic data, Argyle pink diamonds can be classified as two types according to their characteristic Raman spectra. The method of the present invention provides sound basis for the rapid determination of the authenticity of the Argyle pink diamonds by Raman spectroscopy.

2 Claims, 10 Drawing Sheets

RAPID IDENTIFICATION METHOD OF ARGYLE DIAMOND'S ORIGIN BY CHARACTRISTIC RAMAN SPECTRA

BACKGROUND OF THE INVENTION

1. Field of the Invention

The present invention relates to a method of Argyle diamond's origin, and particularly to a rapid identification method of Argyle diamond's origin by characteristic Raman spectra.

2. Related Art

The "pink diamonds" from the Argyle mines in Northern Territory of Australia were first mined in 1985. Argyle pink diamond accounts for 90% of the global pink diamond production, despite that they only found in 1% of the total Argyle repository. The beauty and relative rarity of pink diamonds made them highly valued and desired worldwide. Although they have been discovered from a number of localities around the world, historically their production has been quite sporadic. In the past 20 years, has only one source, the Argyle mine in Australia, produced a consistent supply of pink diamonds, which has given these special gemstones unrivaled commercial importance in the jewelry marketplace. One of the commercial challenges in gem industry today is to quickly identify the origin of pink diamonds-whether they are natural, treated or synthetic ones by means of standard and advanced gemological instruments. In addition, diamonds set in jewelry rings have usually been traded through several business transactions and in general less likely to be traced for its origin. Therefore, how to rapidly identify diamonds' origin scientifically becomes very important issue for diamond traders and appraisal laboratories.

In the past, except for occasional discussions on the occurrence and physical properties, there were few published studies on the gemological properties of pink diamonds by more sophisticated instrument. No matter whether the samples are loose diamonds or jewelry sets, solid data collection and cautious scientific analysis are of utmost importance in providing an objective identification of originality to support the diamond's authenticity.

Although the main elemental component is carbon, difference in trace amount of impurity, defects and the remnant natural radiation make identifying the origin or locality of diamonds particularly difficult. It is almost unlikely to recognize the locality of diamonds through a magnifying lens or a microscope, which may be biased because it relies solely on the appraiser's experience. Consequently, to determine the authenticity of the gemstones without robust scientific evidence would have the shortfall of subjectivity.

SUMMARY OF THE INVENTION

Accordingly, an object of the present invention is to provide a rapid identification method of Argyle diamond's origin by characteristic Raman spectra.

To achieve the above-mentioned object, the method of the present invention comprises steps of providing a Raman spectrometer to collect Raman spectra of multiple sample diamonds under conditions of 785 nm laser excitation, 450 mw laser power, $250 \sim 2,350$ $cm^{-1}$ Spectral Range, spatial resolution >100 µm, and 0.2~3 seconds integration time; and the sample diamonds being identified as type A and type B on the basis of diagnostic features of Raman raw spectra; wherein Raman raw spectra of type A diamonds showing diamond's C—C bonds at 1332 $cm^{-1}$ protrude on a convex-shaped background, and when raw data of type A are processed by a background correction and normalization program, eight distinctive peaks at 640 $cm^{-1}$, 832 $cm^{-1}$, 952 $cm^{-1}$, 1012 $cm^{-1}$, 1225 $cm^{-1}$, 1834 $cm^{-1}$, 1940 $cm^{-1}$, 2120 $cm^{-1}$ are shown up in the spectrum, in addition to the C—C mode at 1332 $cm^{-1}$, the eight peaks being interpreted as fluorescent peaks excited by the incident near-infrared 785 nm laser beam and defining the type A diamonds as Argyle pink diamonds; and when Raman raw spectra of type B diamonds are processed by the background correction and normalization program, eight distinctive peaks at 302 $cm^{-1}$, 339 $cm^{-1}$, 640 $cm^{-1}$, 952 $cm^{-1}$ 1012 $cm^{-1}$ 1250 $cm^{-1}$ 1273 $cm^{-1}$ and 1565 $cm^{-1}$ are shown up in the spectrum of type B diamonds, whereby defining type B diamonds as Argyle pink diamonds.

In one aspect of the present invention, high Raman background fluorescence in Argyle pink diamond is one of the bases for the distinction of their origin.

The method of the present invention utilizes Raman spectroscopy to provide fast and easy differentiation between the Argyle pink diamonds and generic pink diamonds. Furthermore, Raman spectroscopy is the benchmark for determining the origin, especially for fancy-colored gemstones.

BRIEF DESCRIPTION OF THE DRAWINGS

FIG. 2-a shows a Raman spectrum of Argyle diamond Type A;

FIG. 2-b shows overlaid Raman spectra of Type A random choice of 01~10 from ADL-01~ADL-16 (300~2100 $cm^{-1}$-baselined);

FIG. 4-a shows a Raman spectrum of Argyle Diamond Type B;

FIG. 4-b shows overlaid Raman spectra of Type-B random choice of 01~10 from ADL-17~ADL-56;

FIG. 6-a shows Raman spectra of Type IIa-ADR-01, ADR-02, ADR-03 pink diamonds;

FIG. 6-b shows a Raman spectrum of ADR-04 CVD pink diamond treated by irradiation.

DESCRIPTION OF THE PREFERRED EMBODIMENTS

Diamonds used for analysis in the present invention are all provided by Independent Gemological Laboratory (IGL), Australia. These diamonds are mined from the Argyle mines and each one is accompanied by a certificate with a serial number from GIA or GSL for verification, making their originality particularly credible.

There are 56 loose Argyle Diamond samples examined in the present invention. These sample Argyle pink diamonds are numbered as ADL01 to ADL56. Four diamonds set on rings (numbered as ADR01 to ADR04) also provided by IGL are used as a test for their origin.

A Raman system used in the present invention is ProTT-EZRaman-G5 (TSI). All Raman spectra are collected under following conditions: 785 nm laser excitation; 450 mw laser power; $250 \sim 2,350$ $cm^{-1}$ Spectral Range; Spatial Resolution >100 µm; high sensitivity (S/N>10,000); 0.2~3 seconds integration time; the laser spot size is large enough to cover a large area on the tested sample. After the raw spectra are collected, proper data reduction process is adopted to carry out background correction and normalization, in order to obtain the correct signal intensity and optimized baseline and to generate the high quality characteristic Raman peaks. The conditions required for the examination of the samples in the present invention are summarized in Table 1.

Table 1 shows the working conditions of the Raman spectrometer required for the present invention.

| Item | Specification |
| --- | --- |
| Excitation Source | 785 nm laser beam |
| Laser Power | Max. 450 mW |
| Laser Spot Size | >100 µm |
| Spatial Resolution | >100 µm |
| Spectral Range | 250~2,350 $cm^{-1}$ |
| Integration Time | 0.2~3 seconds |
| Sensitivity | S/N ratio > 10,000 |
| Software | Background Correction and Normalization of Raw Data |

Figure 1:
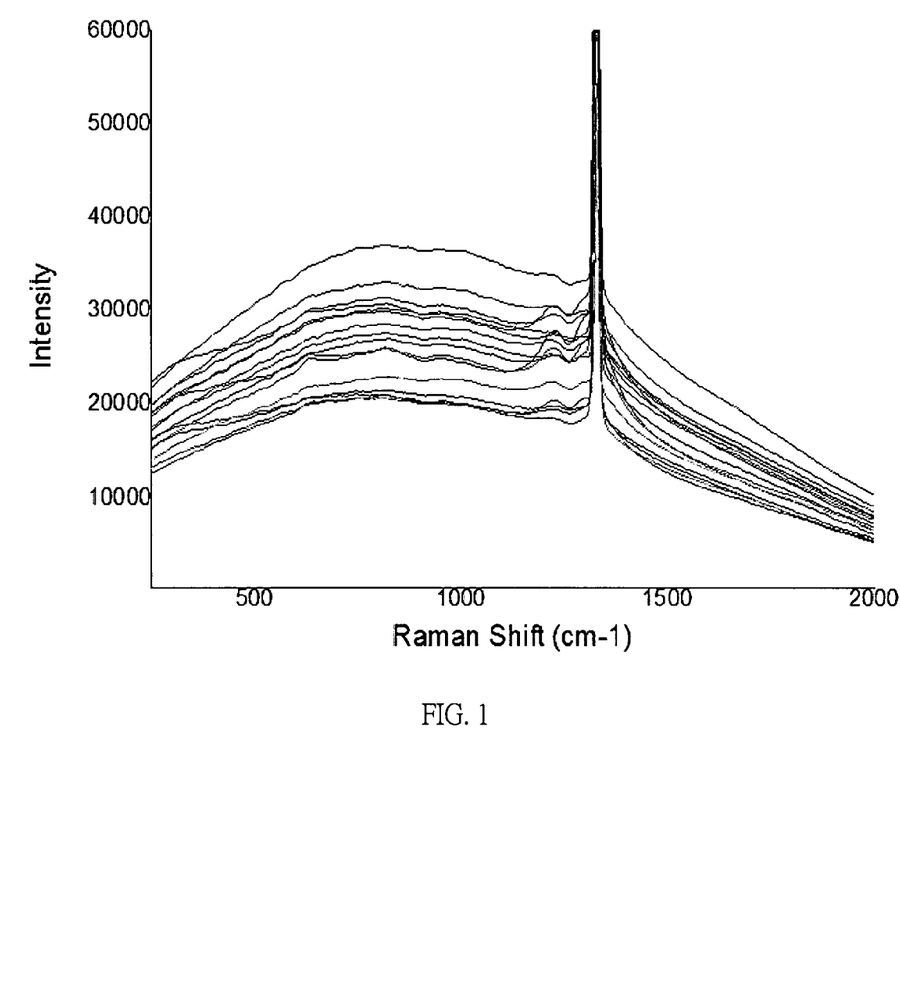
FIG. 1 shows over laid Raman spectra of 16 samples (ADL-01~ADL-16) of Type A.
Figure 2:
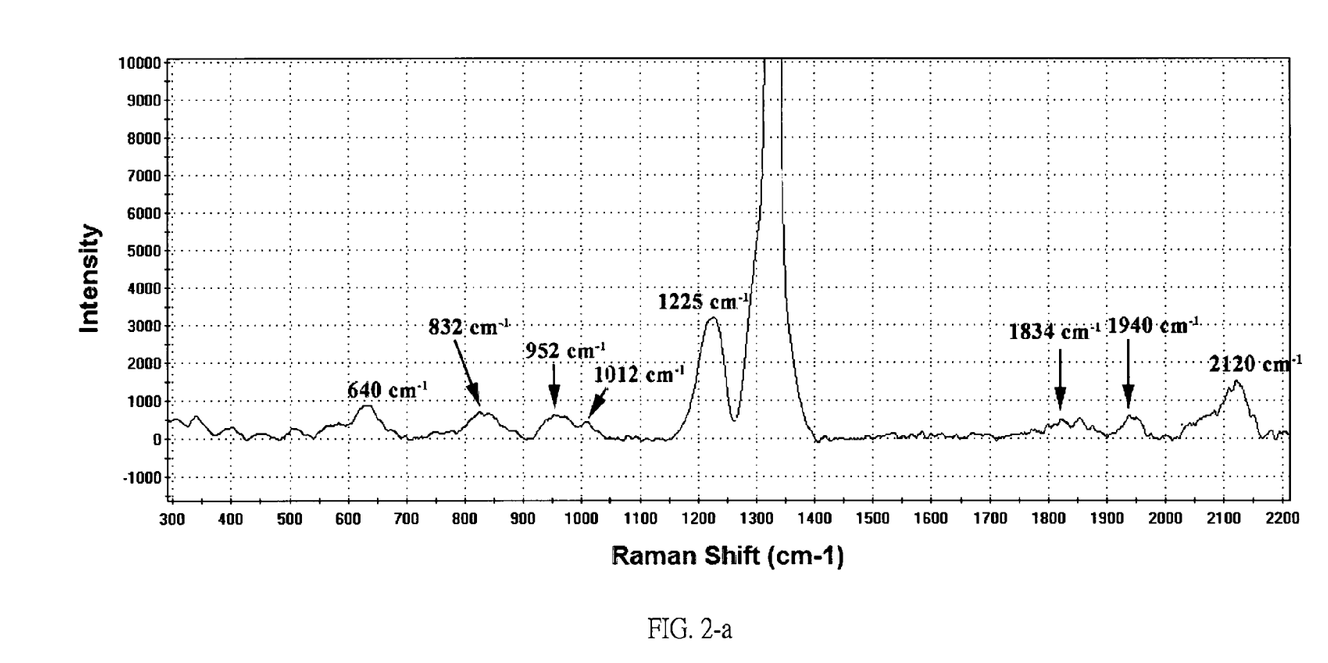

The 56 Argyle pink diamonds examined by Raman spectrometer and the raw data are compiled and classified as two types as Type A and Type B on the basis of the diagnostic feature of Raman raw spectra. Samples of ADL-01~ADL-16 are identified to be Type A. Raman raw spectra of Type A shown in FIG. 1 of their overlaid spectra, illustrating that the diamond's C—C bonds at 1332 $cm^{-1}$ protruding on a convex-shaped background (FIG. 1). When the raw data are processed by background correction and normalization program, it is observed that eight distinctive peaks at 640 $cm^{-1}$, 832 $cm^{-1}$, 952 $cm^{-1}$, 1012 $cm^{-1}$, 1225 $cm^{-1}$, 1834 $cm^{-1}$, 1940 $cm^{-1}$, 2120 $cm^{-1}$ show up in the spectrum, in addition to the C—C mode at 1332 $cm^{-1}$ (FIG. 2-a). These peaks are interpreted as the fluorescent peaks excited by the incident near-infrared 785 nm laser beam. Primarily, the fluorescent peaks found in Argyle pink diamond are due to the lattice defects caused by natural radiation in the Earth's mantle. The presence of these fluorescent peaks is a common feature of the Type A Argyle pink diamonds, which can be seen in overlaid spectra of random samples Type-A01~Type-A10 in FIG. 2-b. Although these fluorescent peaks are not the standard Raman peaks of diamond, their presence along with the characteristic convex background are diagnostic of the Type A Argyle diamonds.

Figure 3:
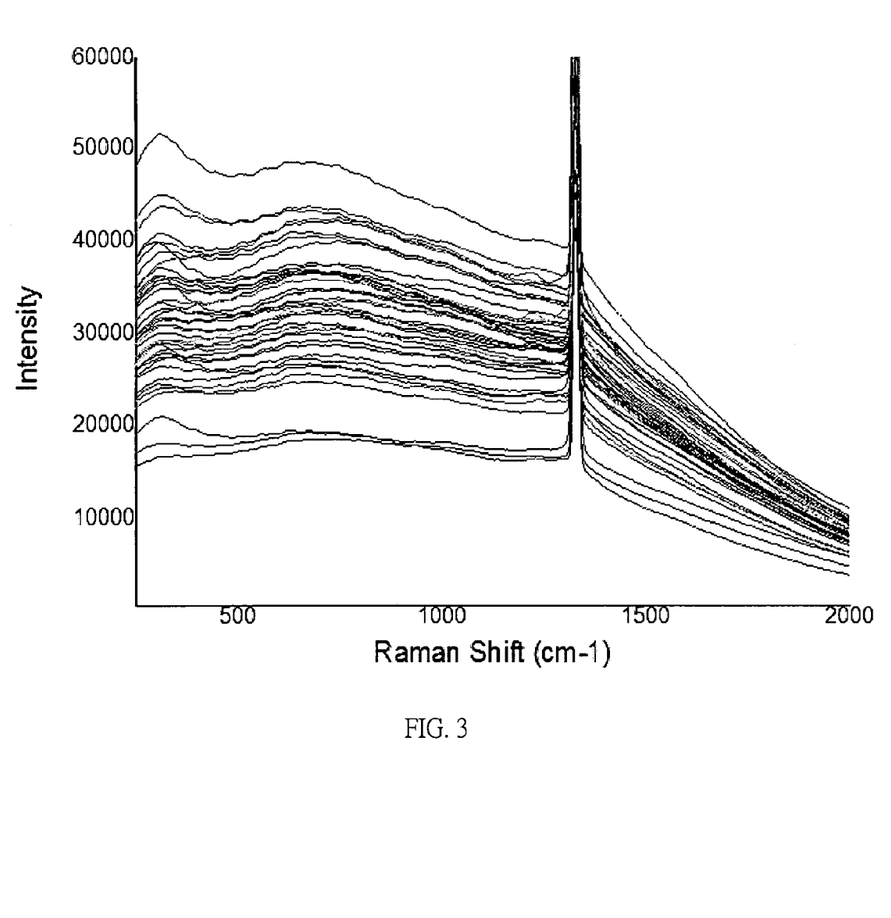
FIG. 3 shows overlaid Raman spectra of 40 samples (ADL-17~ADL-56) of Argyle diamond Type B.
Figure 4:
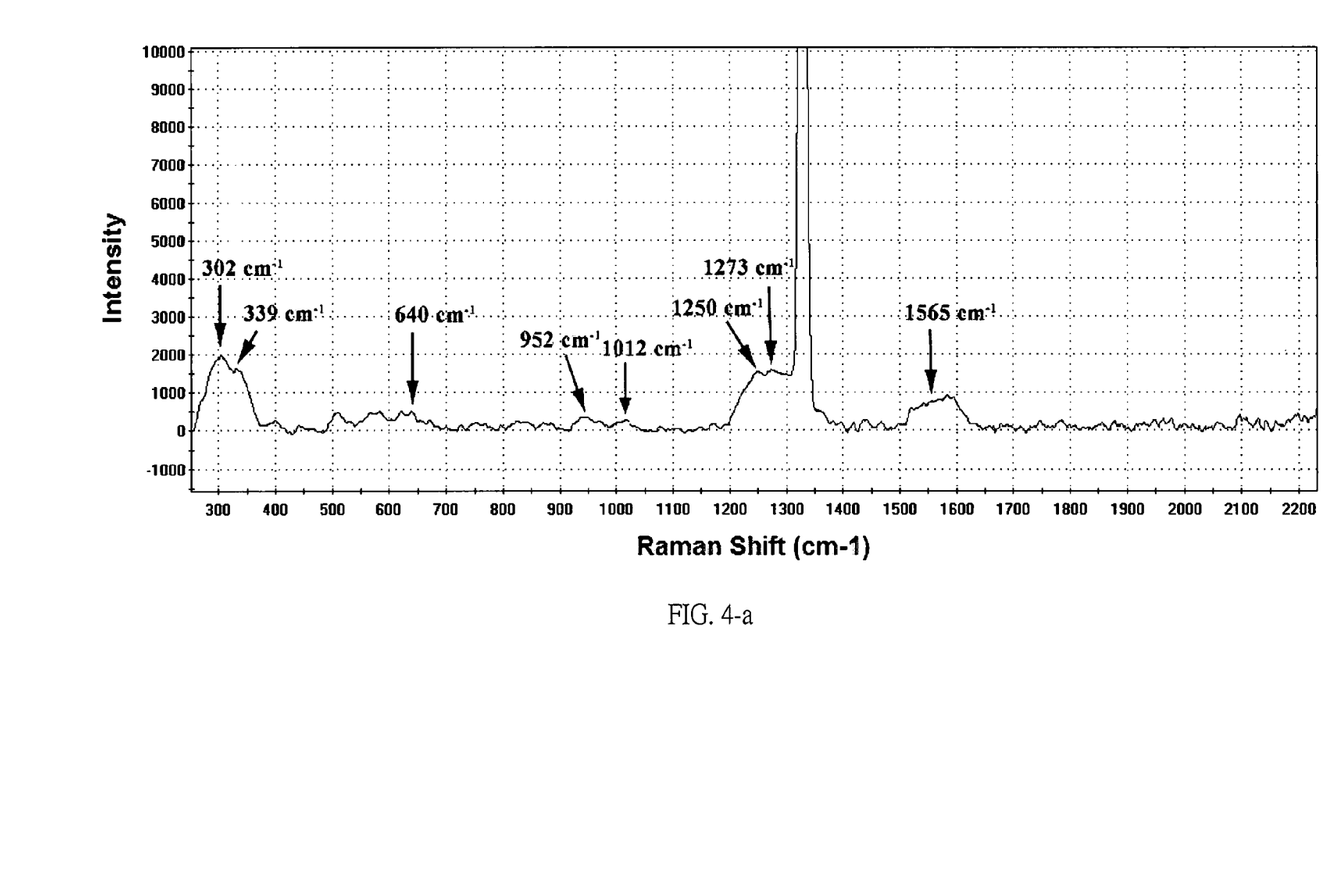

Type B comprises ADL-17~ADL-56 (total 40 samples) from the 56 samples. The Raman raw spectra of Type B Argyle diamonds are shown in FIG. 3 as overlaid spectra. Profound background also shows up for each spectrum, but the shape is different from that of Type A Argyle Diamonds. In contrast, the background is sloping down to the high-wavenumber end of the spectrum with protruding C—C bonds at 1332 $cm^{-1}$ of diamond (FIG. 4-a). When the raw data are processed by background correction and normalization program, it is observed that eight distinctive peaks at 302 $cm^{-1}$, 339 $cm^{-1}$, 640 $cm^{-1}$, 952 $cm^{-1}$, 1012 $cm^{-1}$, 1250 $cm^{-1}$, 1273 $cm^{-1}$, and 1565 $cm^{-1}$ show up in the spectrum, in addition to the C—C mode at 1332 $cm^{-1}$. (FIG. 4-a). These peaks are also interpreted as the fluorescent peaks excited by the incident near-infrared 785 nm laser beam. The Type B Argyle samples display common characteristic fluorescent peaks at 640 $cm^{-1}$, 952 $cm^{-1}$, 1012 $cm^{-1}$ as seen in Type A Argyle diamonds. However, the characteristic peaks at 302 $cm^{-1}$, 339 $cm^{-1}$, 1250 $cm^{-1}$, 1273 $cm^{-1}$, 1565 $cm^{-1}$, which are common feature for Type B Diamonds (FIG. 4-a) are not observed in the Raman spectra of Type A Diamonds. The major characteristic peak is also shifted in the Type B to 1250 $cm^{-1}$, 1273 $cm^{-1}$, differing from the 1225 $cm^{-1}$ peak of Type A.

The presence of these fluorescent peaks is a common feature of the Type B Argyle pink diamonds, which can be seen in overlaid spectra of random samples Type-B01~Type-B10 in FIG. 4-b. Again, although these fluorescent peaks are not the standard Raman peaks of diamond, their presence along with the characteristic sloping down background are diagnostic of the Type B Argyle diamonds.

Figure 5:
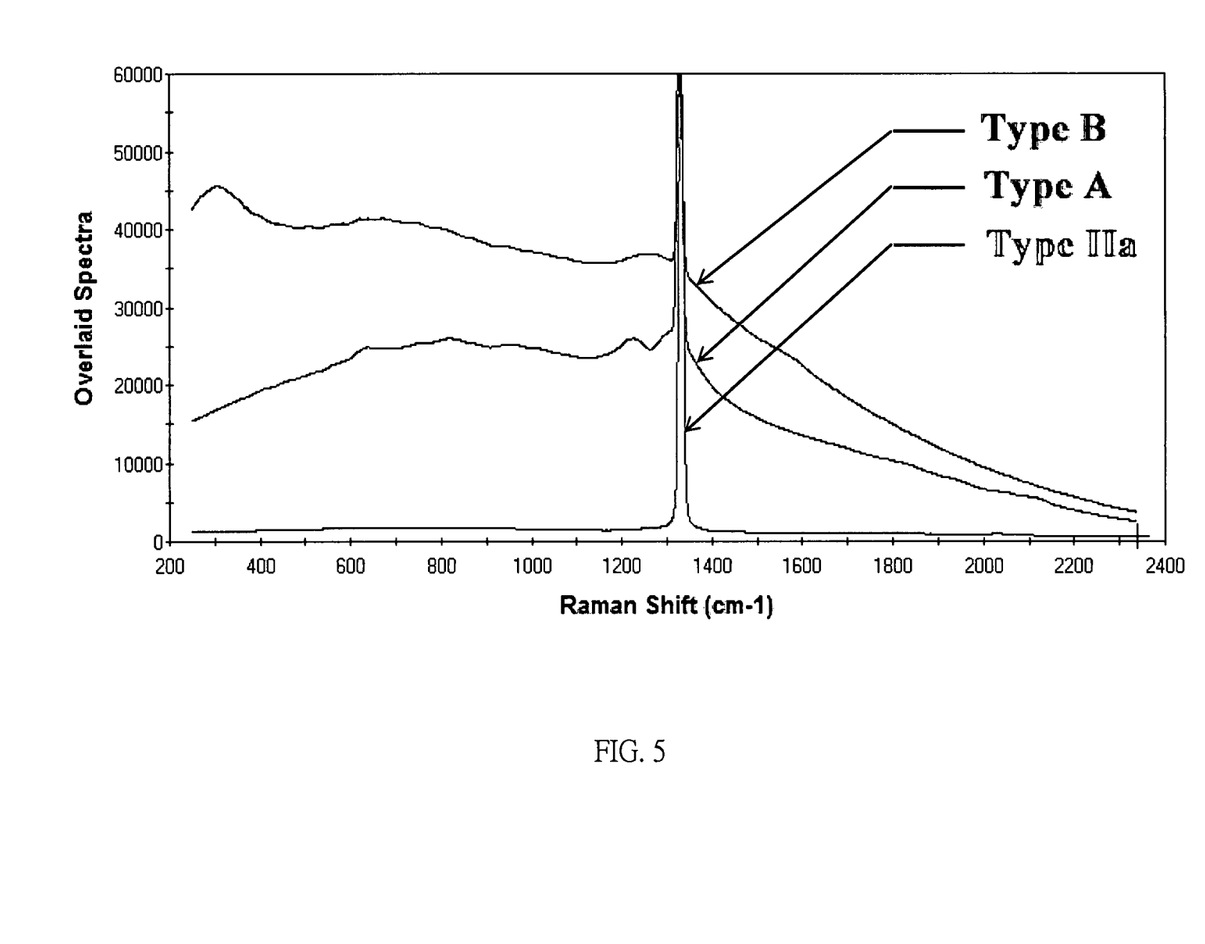
FIG. 5 shows Raman spectra of Raw data of Type IIa, Type A and Type B Pink diamonds.

High Raman background fluorescence in Argyle pink diamond is one of the bases for the distinction of their origin. It is observed that the "Raw Raman spectra" from the three pink diamond samples have very different when overlaid, where the Type IIa pink diamonds are ADR-01~ADR-03, while Type A and Type B spectral pattern represent Raman spectral of the typical Argyle pink diamond (FIG. 5). The specific background pattern of fluorescence observed from Type A and Type B Raman spectrum is the result of natural radiation from the surrounding source rocks of the Argyle ores. This notably high background fluorescence of the Argyle diamond constitutes one of the most important characteristics of the Raman spectra to identify its origin.

Figure 6:
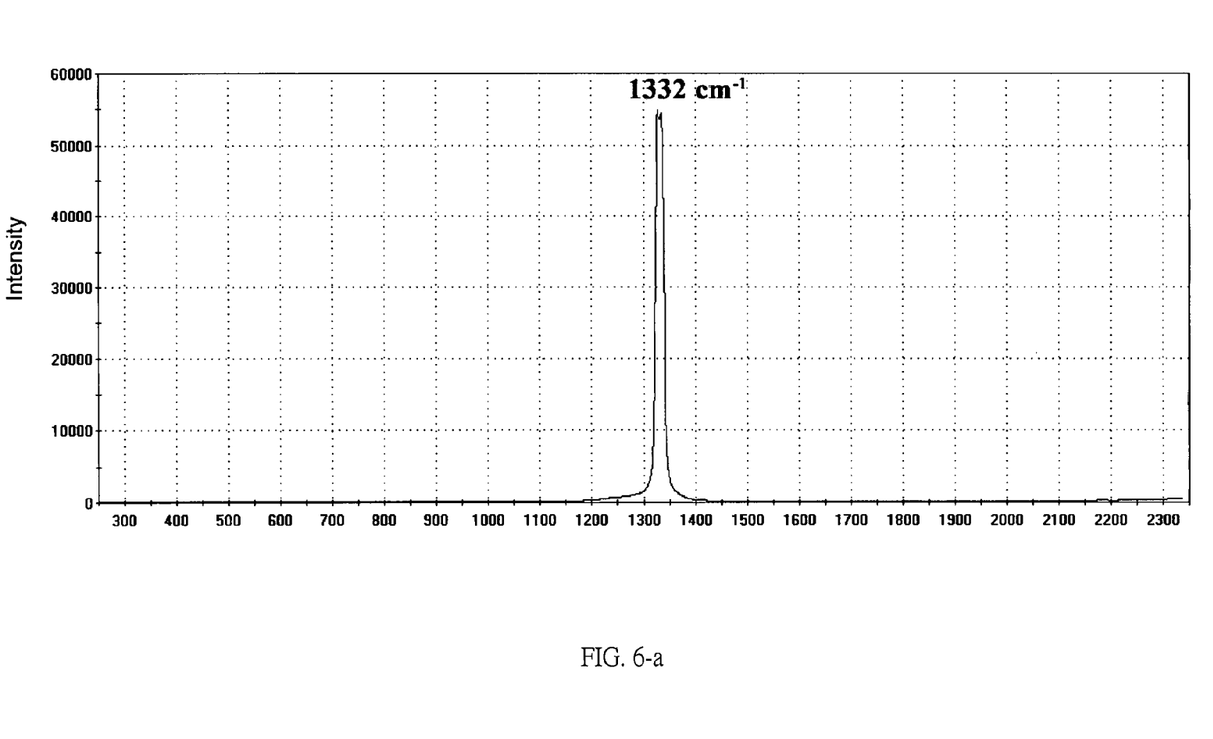

While the 56 loose Argyle diamond samples provided by IGL Australia are supported by serial numbers and certificates from the Australian Argyle mine, the Type A and Type B identified in the present invention displayed slightly different Raman responses. If the serial numbers and certificates from the Argyle mine produced as proof of origin are proven to be dependable, from our scientific analysis of their similarity in the Raman data (original and characteristic peaks), one can hypothesize that both types of the Argyle diamonds are authentic, but from a different mining region of Argyle. The identification method also applies to the Argyle stimulants in the ring sets, such as samples ADR-01, ADR-02, ADR-03 (FIG. 6-a) and ADR-04 (FIG. 6-b), which will be further classified as Type IIa pink diamond and CVD treated by irradiation categories in PCA analysis.

Figure 7:
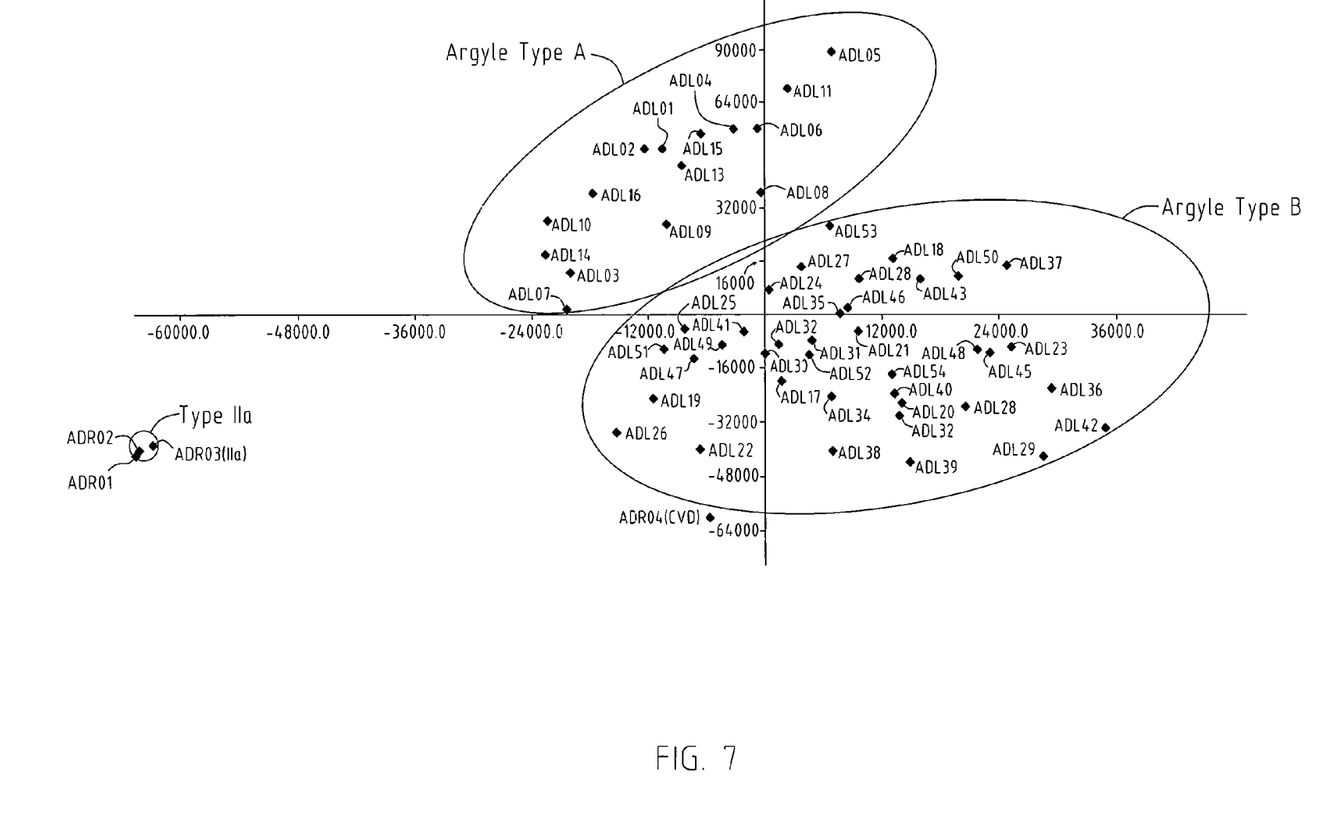
FIG. 7 is a schematic scatter diagram showing PCA distribution plot of samples (250 $cm^{-1}$~1300 $cm^{-1}$).

Principal Component analysis (PCA) is performed over the Raman data sets, with the aim of comparing the pink diamond spectral data in terms of similarities and differences in an unsupervised manner. PCA is conducted over the raw Raman spectra on the spectral range 250~1300 $cm^{-1}$. The results show that the first two principal components (PC-1 and PC-2) covered 99.84% of the variation in spectral data and so these two components are used as the base for further analysis. The third and higher-order principal components (PCs) did not show any clear differentiation among pink diamonds. FIG. 7 is a scatter diagram of component score for the first and second principal component (PC-1, PC-2). This diagram is the most important graph of principal component analysis. The plot gives information about patterns in the Argyle pink diamonds. The score plot for (PC-1, PC-2) is especially useful, since these two components cover almost all variation in the data than any other pair of components. According to the distribution, the samples can be divided into 3 clusters. Objects lying in a given cluster share common features which is distinctive from samples in other clusters. Clusters lying within each red oval loop are relatively similar. A separation among various pink diamonds can be observed along the PC1-axis, which explains the 97.29% of the total variance in the data set. In this case, PCA analysis in 250-1300 $cm^{-1}$ region led to the separation of three main groups, group A (dots in the upper circle shown in FIG. 7), B (dots in the lower circle shown in FIG. 7) and the group of unknown pink diamond rings (dots outside the upper and lower circles in FIG. 7). It is noticed that ADR04, a CVD pink diamond treated by irradiation, lies close to the loop of group B. This is due to the artificial background radiation similar to Argyle natural radiation. Other diamonds set on rings (ADR01, ADR02, ADR03) cluster into a group which is closed to type IIa pink diamond. As for identifying CVD pink diamond and Type IIa pink diamond, it is not the research scope of this article.

Diamonds are one of the most treasured gems, with the pink diamonds commonly referred to as the crown jewel of all diamonds. Amongst the pink diamonds, the Argyle pink diamond is highly desired by collectors and traders for its brilliance and rarity. In the present invention, Raman spectroscopy is utilized to provide fast and easy differentiation between the Argyle pink diamonds and generic pink diamonds. Actually, Raman spectroscopy is the benchmark for determining the origin, especially for fancy-colored gemstones. Raman spectroscopy also can provide an accurate and more detailed categorization, provided that the instrument is of superb quality in sensitivity and resolution. Statistically speaking, a larger sample-pool size will help in producing a more meaningful result. However, in the present invention we are limited by the rarity of the Argyle pink diamonds. Nevertheless, the method of the present invention confirms that Raman spectroscopy can identify Argyle pink diamond and can be applied to identify other precious stones to provide a reliable appraisal, not only to accelerate the identification process, but also to improve the accuracy of identification.

It is understood that the invention may be embodied in other forms within the scope of the claims. Thus the present examples and embodiments are to be considered in all respects as illustrative, and not restrictive, of the invention defined by the claims.

What is claimed is:

1. A rapid identification method of Argyle diamond's origin by characteristic Raman spectra, comprising steps of:
   providing a Raman spectrometer to collect Raman spectra of multiple sample diamonds under conditions of 785 nm laser excitation, 450 mw laser power, 250~2,350 $cm^{-1}$ Spectral Range, spatial resolution >100 μm, and 0.2~3 seconds integration time; and
   the sample diamonds being identified as type A and type B on the basis of diagnostic features of Raman raw spectra;
   wherein Raman raw spectra of type A diamonds showing diamond's C—C bonds at 1332 $cm^{-1}$ protrude on a convex-shaped background, and when raw data of type A diamonds are processed by a background correction and normalization program, eight distinctive peaks at 640 $cm^{-1}$, 832 $cm^{-1}$, 952 $cm^{-1}$, 1012 $cm^{-1}$, 1225 $cm^{-1}$, 1834 $cm^{-1}$, 1940 $cm^{-1}$, 2120 $cm^{-1}$ are shown up in the spectrum, in addition to the C—C mode at 1332 $cm^{-1}$, the eight peaks being interpreted as fluorescent peaks excited by the incident near-infrared 785 nm laser beam and defining the type A diamonds as Argyle pink diamonds; and when Raman raw spectra of type B diamonds are processed by the background correction and normalization program, eight distinctive peaks at 302 $cm^{-1}$, 339 $cm^{-1}$, 640 $cm^{-1}$, 952 $cm^{-1}$, 1012 $cm^{-1}$, 1250 $cm^{-1}$, 1273 $cm^{-1}$, and 1565 $cm^{-1}$ are shown up in the spectrum of type B diamonds, whereby defining type B diamonds as Argyle pink diamonds.

2. The method of claim 1, wherein high Raman background fluorescence in Argyle pink diamond is one of the bases for the distinction of their origin.

* * * * *